(12) United States Patent
Li

(10) Patent No.: US 6,814,730 B2
(45) Date of Patent: Nov. 9, 2004

(54) BALLOON CATHETERS FOR NON-CONTINUOUS LESIONS

(76) Inventor: Hong Li, 4431 Shorepointe Wy, San Diego, CA (US) 92130

( * ) Notice: Subject to any disclaimer, the term of this patent is extended or adjusted under 35 U.S.C. 154(b) by 99 days.

(21) Appl. No.: 10/252,231

(22) Filed: Sep. 23, 2002

(65) Prior Publication Data

US 2003/0069620 A1 Apr. 10, 2003

Related U.S. Application Data

(60) Provisional application No. 60/327,991, filed on Oct. 9, 2001.

(51) Int. Cl.$^7$ ............................................... A61B 18/04
(52) U.S. Cl. ............................. 606/28; 606/27; 607/96; 607/105; 607/113
(58) Field of Search ............................... 606/28, 27, 33, 606/41; 601/96, 105, 113

(56) References Cited

U.S. PATENT DOCUMENTS

| | | | |
|---|---|---|---|
| 5,250,070 A | * 10/1993 | Parodi | ........................ 606/194 |
| 5,454,782 A | 10/1995 | Perkins | |
| 5,925,038 A | * 7/1999 | Panescu et al. | ................ 606/41 |
| 6,009,877 A | 1/2000 | Edwards | |
| 6,012,457 A | 1/2000 | Lesh | |
| 6,073,052 A | 6/2000 | Zelickson | |
| 6,656,209 B1 | * 12/2003 | Ginsburg | .................... 607/106 |

* cited by examiner

Primary Examiner—Lee S. Cohen
(74) Attorney, Agent, or Firm—Charles C. Logan, II

(57) ABSTRACT

Balloon catheters according to the present invention have surface contours with protrusions and grooves to make non-continuous lesions. There is a heating element inside the balloon. The balloon will be filled with a fluid before ablation to expand the balloon for tissue contact, and to transfer heating energy from the heating element to the tissue in contact with the balloon. Since the balloon surface has contours with grooves and protrusions, the tissue contact will not be continuous along the balloon surfaces, and therefore the ablation on the tissue will not be continuous. The energy transmitter can be ultrasound transducer, electrical resistant heater, and microwave antenna.

23 Claims, 4 Drawing Sheets

BALLOON CATHETERS FOR NON-CONTINUOUS LESIONS

CROSS-RELATED APPLICATION

This application is the formal application for the provisional application with the same title, filed on Oct. 09, 2001 by Hong Li (application number 60/327,991, confirmation number 5947).

FIELD AND BACKGROUND OF THE INVENTION

The present invention relates to minimum invasive balloon catheters for non-continuous lesions on body tissues, and in particular, on sphincter tissues of body lumen.

In the past, heat induced lesions around a body lumen has been used to shrink the body lumen to treat incontinence. And discontinuous lesions evenly distributed around a body lumen circumference was made to have some viable tissues left between ablated tissues to maintain some elasticity for opening and close, while the overall lumen section was contracted after ablation.

Radio frequency (RF) ablation catheters has been used to ablate sphincter tissues in body lumen, to treat deceases such as gastro esophageal reflux, fecal incontinence and urinary stress incontinence. Although RF catheters can generate sufficient heat to cause sphincter tissue to shrink, there are three drawbacks of RF ablation to shrink a body lumen. The first is that it often results in tissue charring because RF electrode edges have high current density and generate much higher heat than non-edged areas of the electrode. So RF electrodes have to be cooled by a fluid during ablation. The second is that needle electrodes had to be used to make discontinuous lesions and minimize mucosa damage. The risk of the needles is that it can perforate a body lumen. The third is that the needle electrodes could not make many lesions at once.

Balloon catheters filled with fluid heated electrically were used to ablate uterus. And balloon catheters heated by ultrasound transducer were used to ablate cardiac tissue. These balloon catheters have advantages of evenly heating around balloon surface without tissue charring, and good tissue contact in body lumen, and ablating large areas at the same time. Yet these balloon catheters have not been used to shrink body lumen by ablating sphincter tissue. One of the reasons for that could be due to the fact that the balloon catheters in the prior arts tend to make continuous lesions especially circumferencely around a body lumen, which is not desired.

OBJECT AND BRIEF SUMMARY OF THE INVENTION

Objectives of this invention are to make balloon ablation catheters which can make non-continuous multiple lesions over large areas of body lumen for tightening.

The balloon catheters according to the present invention have surface contours with protrusions and grooves to make non-continuous lesions. There is a heating element inside the balloon. The balloon will be filled with a fluid before ablation to expand the balloon for tissue contact in a body lumen, and to transfer heating energy from the heating element to the tissue in contact with the balloon. Since the balloon surface has contours with grooves and protrusions, the tissue contact will not be continuous along the balloon surfaces, and therefore the ablation on the tissue will not be continuous.

Balloon catheters have advantages of no char and no perforation on tissues when making lesions, and many lesions made at the same time on large areas with controlled distances.

DETAILED DESCRIPTION

Figure 1:
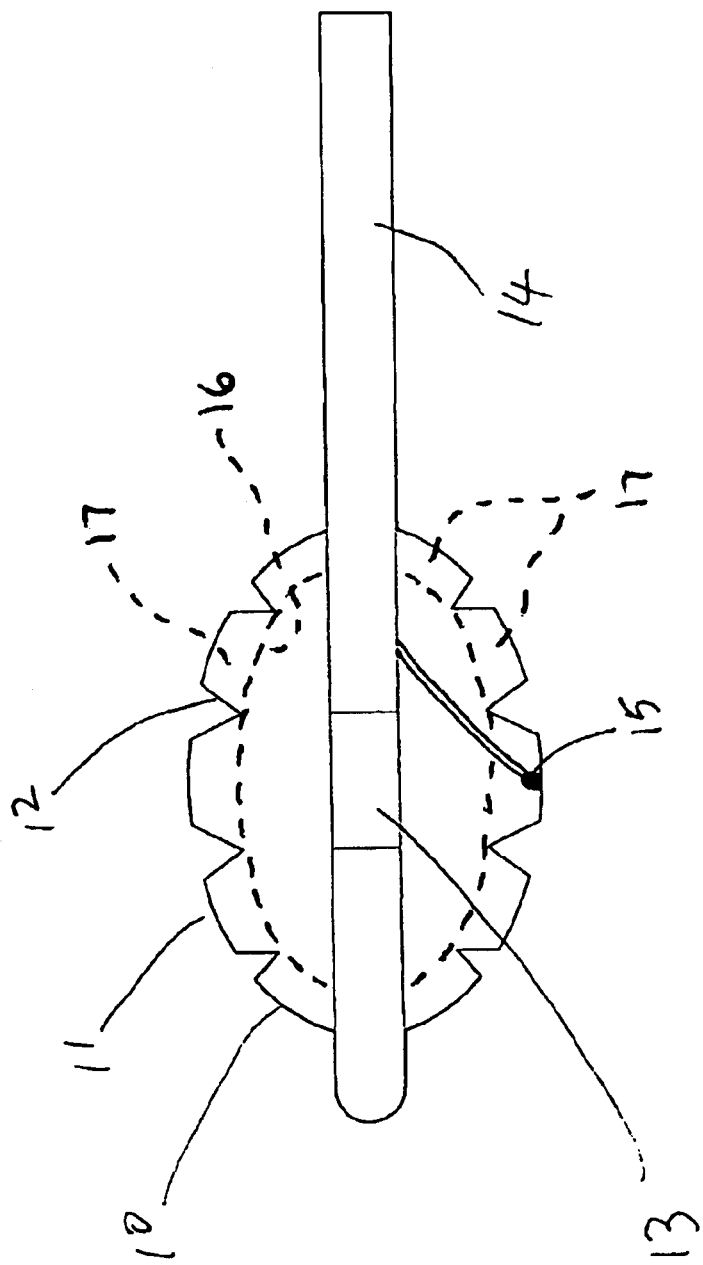
FIG. 1 is a cross section view of the balloon catheter distal section, having surface contours with grooves and protrusions. It is also shown in the figure that a heating element is mounted on the catheter shaft inside the balloon.

As illustrated in FIG. 1, a balloon catheter for tissue ablation has a heating element 13 at distal section of the catheter. The heating element is covered by a balloon 10. The balloon can be expanded and contracted by injection and extraction of a fluid through the catheter shaft 14. Balloon expansion is for tissue contact, and balloon contraction is good for moving the catheter in and out of body lumen. Heat is conducted from the heating element through the fluid and the balloon to the body tissue in contacted with the balloon surface. Mainly the tissue in good contact with the balloon surface will be ablated due to good heat transfer.

The main feature of the present invention is that the catheter balloon has surface contours with protrusions 11 and grooves 12 for discrete ablations. The inflated balloon defines a main chamber 16 and the protrusions are hollow (see FIG. 1) to form sub-chambers 17. Only the protruded areas of the balloon will be in good contact with the tissue to ensure good heat transfer and ablation. The tissue facing the grooved areas will have no contact to the balloon surface, and therefore no good heat transfer and lesions. The grooved areas will be filled with body fluid or air, and therefore the heat inside the balloon cannot be directly transferred on to the tissue in the areas. Therefore, the balloon catheter will make non-continuous lesions circumferencely around a body lumen.

There is a need to create discontinuous lesions such as in a body lumen, to tighten it without permanent impairment of the body lumen's ability for normal relax and close, for treatment of deceases such as fecal incontinence, urinary stress incontinence, gastro esophageal reflux disease, and morbid obesity. Discontinuous lesions can achieve the goal of tightening a body lumen and reducing frequency of relaxation, while maintaining normal lumen function of relax and close by leaving viable tissues in between lesions. Continuous lesion on the other hand, especially continuous circumference lesion, could permanently destroy a body lumen's normal function of relax and close.

Discontinuous lesions can be made on many tissues in body lumens such as nose, esophageal, ostium cardiacum, stomach, pylori, intestine, anus, urethra, and bladder outlet, for tissue remodeling, tightening, and nerve ablation.

Figure 2:
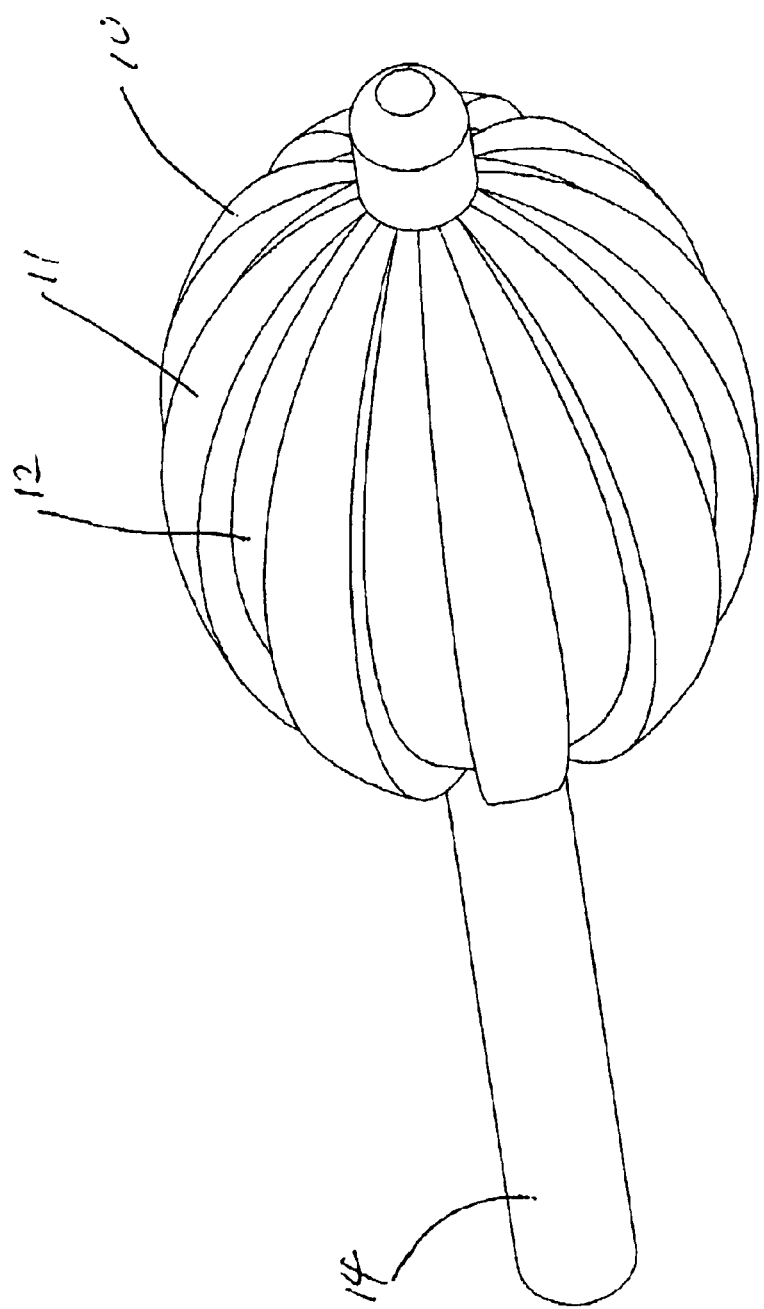
FIG. 2 illustrates a pattern of balloon surface contours with elongated protrusions and grooves aligned parallel to catheter axis.
Figure 3:
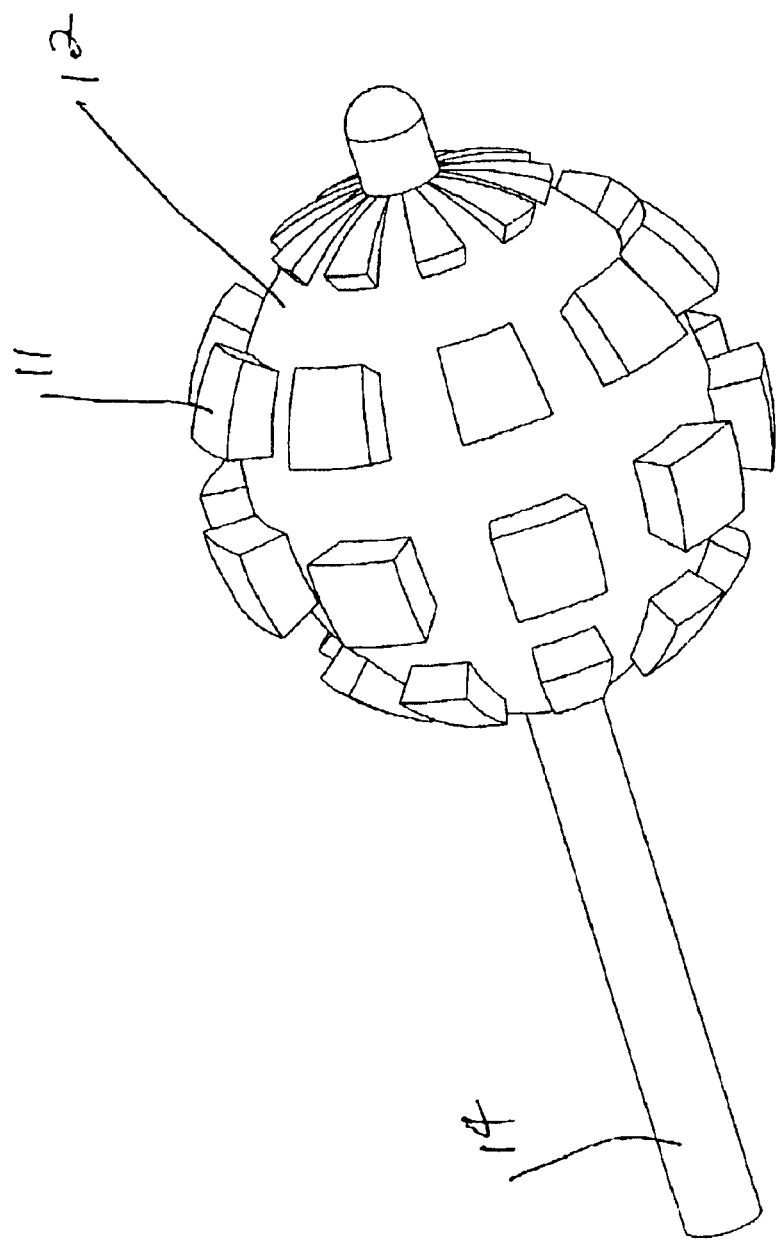
FIG. 3 shows a pattern of balloon surface contours with irregularly shaped protrusions and grooves aligned both parallel to and perpendicular to the catheter axis.
Figure 4:
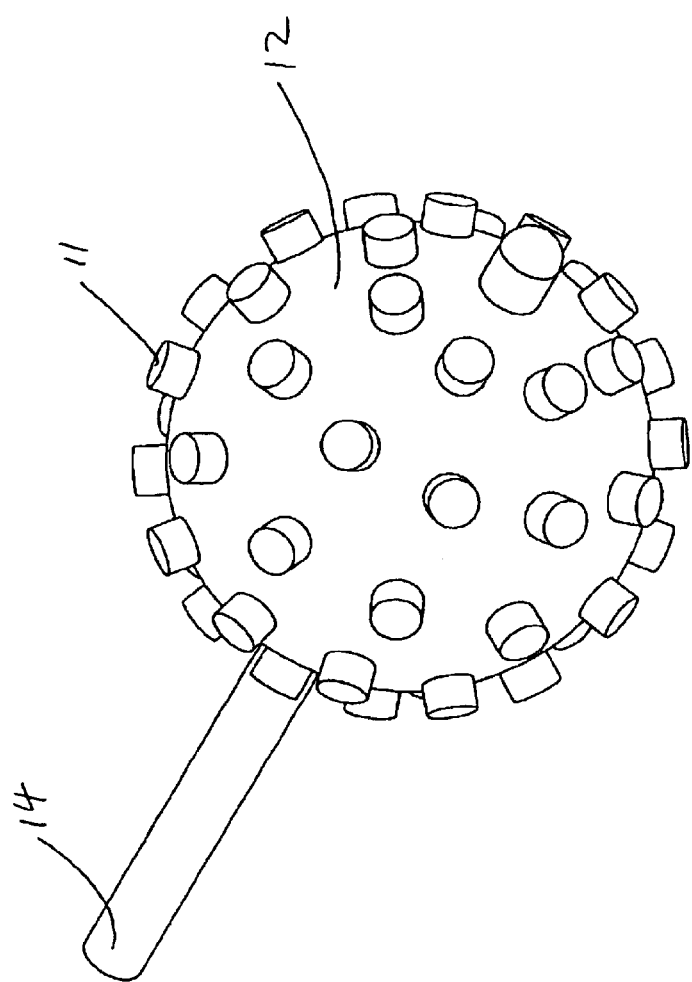
FIG. 4 shows a random pattern of many protruded round areas on the balloon surface.

The protrusions and the grooves can be arranged on the balloon surfaces in many different patterns to achieve different lesion patterns. They can be elongated as illustrated in FIG. 2, or non-elongated as shown in FIGS. 3 and 4. They can be placed evenly in distance, or in angle (FIG. 2). They can be aligned in any direction, such as parallel to the catheter axis, or with an angle to the axis. Or they can be placed randomly on the balloon surface.

The balloons with protrusions and the grooves on the surface can be molded with plastics such as Nylon, Pebax, and PET.

The heating element 13 can be an electrical resistant, microwave antenna, or an ultrasound transducer. Thermocouples 13 can be placed to the balloon surface, the heating element, and in the fluid. The fluid can be water, or saline for good heat conduction and biocompatibility.

I claim:

1. A medical device used to circumferentially ablate the interior surface of hollow human body lumen comprising:
    a balloon catheter having an elongated tubular shaft having a catheter axis and a distal end; said tubular shaft providing a fluid passageway;
    an inflatable balloon attached to said tubular shaft adjacent said distal end; said balloon having an outer surface and an inner surface that defines a main chamber that is in communication with said fluid passageway of said tubular shaft;
    said outer surface of said balloon having a configuration defined by multiple outwardly extending protrusions around said outer surface; said protrusions being hollow to form sub-chambers that are in communication with said main chamber of said balloon; the outer surface distance between said protrusions define grooves whereby when said balloon is inflated by a pressurized fluid in a hollow human body lumen a sufficient amount to press said outer surfaces of said protrusions against the interior tissue surface of said lumen, said grooves will provide passageways that prevent complete blockage of said hollow body lumen; when the fluid is heated to a temperature high enough for tissue ablation, discontinuous lesions will be produced on the interior surface of the tissue in said lumen where said protrusions contact said tissue.

2. A medical device as recited in claim 1 wherein said protrusions have an elongated configuration and said grooves between said protrusions are also elongated.

3. A medical device as recited in claim 2 wherein said elongated protrusions and grooves are parallel to said catheter axis.

4. A medical device as recited in claim 2 wherein said elongated protrusion and grooves are non-parallel to said catheter axis.

5. A medical device as recited in claim 1 wherein said protrusions are non-elongated.

6. A medical device as recited in claim 1 wherein said protrusions and grooves are symmetrically oriented on said outer surface of said balloon.

7. A medical device as recited in claim 1 wherein said protrusions are randomly oriented on said outer surface of said balloon.

8. A medical device as recited in claim 1 further comprising heating means for heating a pressurized fluid when it is pumped into said balloon.

9. A medical device as recited in claim 8 wherein said heating means is an electrical resistant heater.

10. A medical device as recited in claim 8 wherein said heating means is a microwave antenna.

11. A medical device as recited in claim 8 wherein said heating means is an ultrasound transducer from which both ultrasound wave and heat are transfered through the fluid to body tissue in contact with said outer surface of said protrusions for ablation.

12. A medical device as recited in claim 1 further comprising at least one thermocouple attached to said balloon surface for temperature measurement.

13. A method of ablating body lumen tissue of nose, esophageal, ostium cardiacum, stomach, pylori, intestine, anus, urethra and bladder outlet, the method comprising the following steps:
    (A). providing a balloon catheter having an elongated tubular shaft having a catheter axis and a distal end, said tubular shaft providing a fluid passageway; an inflatable balloon attached to said tubular shaft adjacent said distal end, said balloon having an outer surface and an inner surface that defines a main chamber that is in communication with said fluid passageway of said tubular shaft; said outer surface of said balloon having a configuration defined by multiple outwardly extending protrusions around said outer surface, said protrusions being hollow to form sub-chambers that are in communication with said main chamber of said balloon; the outer surface distance between said protrusions define grooves;
    (B). inserting said balloon catheter into a body lumen to be treated;
    (C). inflating said balloon with a sufficient amount of fluid to press said outer surfaces of said protrusions against the interior tissue surface of said lumen; said grooves providing passageways that prevent complete blockage of said hollow body lumen; and
    (D). heating said fluid to a temperature high enough for tissue ablation producing multiple discontinuous lesions on the interior surface of said tissue in said lumen where said protrusions contact said tissue.

14. The method as recited in claim 13 wherein said protrusions of said balloon catheter have an elongated configuration and said grooves between said protrusions are also elongated.

15. The method as recited in claim 14 wherein said elongated protrusions and grooves are parallel to said catheter axis.

16. The method as recited in claim 14 wherein said elongated protrusions and grooves are non-parallel to said catheter axis.

17. The method as recited in claim 14 wherein said protrusions are non-elongated.

18. The method as recited in claim 14 wherein said protrusions and grooves are symmetrically oriented on said outer surface of said balloon.

19. The method as recited in claim 14 wherein said protrusions are randomly oriented on said outer surface of said balloon.

20. The method as recited in claim 14 wherein the fluid is heated by an electrical resistant heater in said balloon.

21. The method as recited in claim 14 wherein the fluid is heated by an electric microwave antenna in said balloon.

22. The method as recited in claim 14 wherein the fluid is heated by an ultrasound transducer from which both ultrasound wave and heat are transfered through said fluid to body tissue in contact with said outer surface of said protrusions for ablation.

23. The method as recited in claim 14 wherein said balloon catheter further comprises at least one thermocouple attached to said balloon surface for temperature measurement.

* * * * *